United States Patent [19]
Zhang et al.

[11] Patent Number: 6,018,101
[45] Date of Patent: Jan. 25, 2000

[54] METHOD USING MALE STERILITY AND A MARKER TO PRODUCE HYBRID SEEDS AND PLANTS

[75] Inventors: Xingping Zhang, Rocky Ford, Colo.; Billy B. Rhodes, Central, S.C.

[73] Assignee: Clemson University, Clemson, S.C.

[21] Appl. No.: 08/796,176

[22] Filed: Feb. 7, 1997

Related U.S. Application Data

[60] Provisional application No. 60/011,380, Feb. 9, 1996.

[51] Int. Cl.$^7$ ...................................... A01H 1/04
[52] U.S. Cl. ......................... 800/274; 800/260; 800/266; 800/271; 800/308
[58] Field of Search ................................... 47/58, DIG. 1; 800/200, 274, 271, 266, 260, 308, 307, 309, 310

[56] References Cited

U.S. PATENT DOCUMENTS

| | | | |
|---|---|---|---|
| 3,842,538 | 10/1974 | Barabas ........................................ | 47/58 |
| 4,326,358 | 4/1982 | Lawrence, Jr. et al. . | |
| 4,351,130 | 9/1982 | Rutger et al. . | |
| 4,378,655 | 4/1983 | Johnson . | |
| 4,727,219 | 2/1988 | Brar et al. ................................... | 800/1 |
| 5,007,198 | 4/1991 | Gray et al. . | |

OTHER PUBLICATIONS

McCreight. Selecting male sterile muskmelons: phenotypic differences of anthers prior to anthesis. Hortscience. vol. 18, No. 4, p. 564, 1983.

Nugent. The genetic relationship of virescent, yellow–green, glabrous, and halo mutants in muskmelon. Hortscience. vol. 15, No. 6, p. 804–805, 1980.

Rhodes. Genes affecting foliage color in watermelon. The Journal of Heredity. vol. 77, pp. 134–135, 1986.

Burton et al. A method for production of experimental quantities of hybrid soybean seed. Crop Science. vol. 23, pp. 388–390, 1983.

Rao et al. Applications of Genic Male Sterility in Plant Breeding, Plant Breeding, vol. 105, pp. 1–25, 1990.

Mohr et al 1955 $F_1$ Hybrid Watermelons from Open–Pollinated Seed by Use of a Genetic Marker. Proc. Amer. Soc. Hort. Sci. 65:399–404.

Rao, M.K. et al 1990. Applications of Genetic Male Sterility in Plant Breeding. Plant Breeding 105:1–25.

*Primary Examiner*—Gary Benzion
*Assistant Examiner*—Melissa L. Kimball
*Attorney, Agent, or Firm*—Dority & Manning, P.A.

[57] ABSTRACT

A method is provided for efficiently producing superior hybrid seed and plants. The method uses a genetic mechanism for ensuring high percentages of natural cross-pollination and combines this mechanism with a genetically conferred morphological trait that allows recognition of desirable genotypes at an early development stage. The genetic mechanism for ensuring high percentages of cross-pollination is male-sterile, a recessive genetic mutant. Thus, the method includes protocols for developing genetic male-sterile (ms) lines. The genetically conferred morphological trait that allows recognition of desirable genotypes at an early development stage is a seedling marker. Thus, the method includes protocols for developing genetic male-sterile (ms) lines with a seedling marker. In watermelon for example, the seedling marker can be a conditionally unfit mutant such as juvenile-albino (ja).

31 Claims, No Drawings

METHOD USING MALE STERILITY AND A MARKER TO PRODUCE HYBRID SEEDS AND PLANTS

The present application is based on a provisional application Serial No. 60/011,380 filed Feb. 9, 1996.

BACKGROUND OF THE INVENTION

The present invention relates to methods of producing hybrid seed in commercial quantities and more particularly to methods using a male-sterile gene.

Hybrid varieties are superior to common open-pollinated varieties. However, hybrid seeds are much more expensive than open-pollinated seeds. For example, hybrid watermelon seed costs ten (for diploids) to one hundred (for triploids) times the cost of open-pollinated seed. One reason hybrid seed is so much more expensive than open-pollinated varieties is because commercial production of hybrid seed requires hand pollination of the flowers of the parent plants that produce the hybrid seed. The seed produced using hand-pollination techniques is estimated to be about fifteen times more expensive than seed produced using open-pollinated methods that rely on natural cross-pollination. Hand-pollination techniques require human visitation to the same female flower on separate days, the concurrent careful protection of female flowers and pollen and/or male flowers, a high degree of skill in thorough pollination of each part of the stigma, and a second covering and marking of the female flower. Considerable skill is required to recognize female flowers that are "ready" for pollination. Moreover, these procedures must be performed at specific times of the day, ideally covering flower buds in the late afternoon and pollinating flowers in the early morning.

One alternative technique demonstrated for watermelon by Mohr et al, *Proc. Amer. Soc. Hort. Sci.* 65:399–404 (1955), which is hereby incorporated herein by this reference, involves using an incompletely dominant genetic marker in the seed parent line that is interplanted with the pollen parent line and relying on natural cross-pollination to effect hybridization. The recessive genetic marker must express itself in the seedling stage so that it permits separation of hybrid plants from the inbred plants that result from self-pollination. The cost-effectiveness of this technique depends on achieving a high percentage of cross-pollination in order to avoid heavy rates of seeding and of thinning non-hybrid plants from the field. Watermelon is monoecious and thus a good candidate for achieving high rates of natural cross-pollination by interplanting the parent lines. However, the Mohr et al method produced a maximum hybrid percentage yield of only 36%.

The 36% yield of the Mohr et al method is unacceptable for commercial hybrid seed, and brings to mind another reason for the high cost of producing hybrid seed in commercial quantities. That reason is the high cost of testing the lots of hybrid seed to determine the percentage of seed that is the desired hybrid variety. Before selling the hybrid seed to the farmer or grower, the hybrid seed producer must conduct testing of each lot of hybrid seed to determine what percentage of the seed will grow out as the hybrid variety. In conducting this purity testing, about 200 plants will need to be allowed to grow out for two to three months for each lot of the hybrid seed. For watermelon, this planting will require about 25 square feet of isolated field for each of the 200 plants. Moreover, during this two to three month testing period, the seed producer will be unable to sell the hybrid seed undergoing testing, thus delaying recoupment of the investment required to produce the hybrid seed being tested.

Other ways of potentially increasing the percentage of cross-pollination suggested by Mohr et al include: (1) rapid removal of easily accessible staminate flowers from the seed parent line without attempting the time-consuming process of completely eliminating them; (2) use of certain chemical growth regulators that are effective in reducing the ratio of staminate to pistillate flowers in other similar species of plants; (3) optimizing the plant spacing and arrangement for maximum cross-pollination; (4) increasing the population of pollinating insects such as honeybees.

Moreover, the Mohr et al method produced inbreds that were as vigorous as the hybrids and could not be recognized at the cotyledon stage. This raises another concern for the producers and users of hybrid seed in commercial quantities. This concern relates to eliminating off-types in the parent plants used to produce the hybrid variety. To determine whether the parents are pure inbreds, it is necessary to grow out the plants to full maturity, by which time there already may have been cross-pollination with off-types. Because of the presence of off-types, harvesting must be performed selectively from plants that are not off-types. Such selective harvesting is very time-consuming, labor-intensive and expensive.

Besides the Mohr et al method, another alternative technique for watermelon was reported by Watts *Proc. Amer. Soc. Hort. Sci.* 81:498–505 (1962), which is hereby incorporated herein by this reference, and suggested that a male-sterile character with a distinctive seedling marker would simplify the problem of hybrid seed production. Watts *Proc. Amer. Soc. Hort. Sci.* 91:579–583 (1967), which is hereby incorporated herein by this reference, concluded that a single recessive gene ($ms_g$) controlled the male-sterile and glabrous characters in the gamma-ray-induced mutant from the "Sugar Baby" variety of watermelon. However, commercial seed production was not feasible because the gene caused female-sterility (partial to severe) in the diploid state and almost complete female-sterility in the tetraploid state. Moreover, fully acceptable melon quality had not been coupled with strong resistance to fusarium wilt and resistance to anthracnose.

OBJECTS AND SUMMARY OF THE INVENTION

It is a principal object of the present invention to provide a method that reduces the cost of producing hybrid seed and plants.

It is another principal object of the present invention to provide a method that reduces the labor needed to produce hybrid seed and plants.

It is still another principal object of the present invention to provide a method that permits open pollination of the two parent lines rather than hand pollination, thereby reducing the cost of producing hybrid seed and plants.

It is a further principal object of the present invention to provide a method that simplifies genetic purity testing of hybrid seed and reduces the time and space needed for such testing.

It is a still further principal object of the present invention to provide a method that uses a marker, which expresses early, to simplify and reduce the cost of genetic purity testing of hybrid seed.

It is yet another principal object of the present invention to provide a method that enables seedsmen and plant breeders to monitor and eliminate any off-types in the seed parent in an early stage of plant development.

It is yet a further principal object of the present invention to provide a method that uses a marker, which expresses early, to simplify and reduce the cost of enabling seedsmen and plant breeders to monitor and eliminate any off-types in the seed parent in an early stage of plant development.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, a method is provided for efficiently producing superior hybrid seed and plants. The method uses a genetic mechanism for ensuring high percentages of natural cross-pollination and combines this mechanism with a genetically is conferred morphological trait that allows recognition of desirable genotypes at an early development stage. The genetic mechanism for ensuring high percentages of cross-pollination is male-sterile, a recessive genetic mutant. Thus, the method includes protocols for developing genetic male-sterile (ms) lines. The genetically conferred morphological trait that allows recognition of desirable genotypes at an early development stage is a seedling marker. Thus, the method includes protocols for developing genetic male-sterile (ms) lines with a seedling marker. In watermelon for example, the seedling marker can be a conditionally unfit mutant such as juvenile-albino (ja). The conditionally unfit mutants selected for the present invention are believed to be superior to the genetic mutant used in previous methods such as Mohr et al because the conditionally unfit mutant allows hybrids to be distinguished more easily from inbreds, which can be eliminated. Moreover, the double recessive genic mutants of the present invention are superior to previous methods like Watts because female fertility, vigor and productivity are not adversely affected.

DETAILED DESCRIPTION OF THE PREFERRED EMBODIMENTS

Reference now will be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. The same numerals are assigned to the same components throughout the drawings and description.

This description uses gene nomenclature accepted by the Cucurbit Genetics Cooperative as it appears in the *Cucurbit Genetics Cooperative Report* 18:85 (1995), which is hereby incorporated herein by this reference. In this gene nomenclature, genes are symbolized by italicized Roman letters. If a mutant gene is recessive to the normal type, then the symbol and name of the mutant gene appear in lower case letters. If the mutant gene is dominant, then the first letter of the symbol and the first letter of the name appear in upper case letters. The normal allele in a chromosome can be represented by a simple plus sign (+). However, if needed for clarity, the normal allele in a chromosome can be represented by the symbol of the mutant gene with a plus sign as a superscript. An hyphen (-) following the symbol means that the gene may be a dominant or recessive allele at that site on the chromosome. For example: $^+$=normal allele when inserted as a superscript on the italicized symbol for the locus.

ms=a recessive mutant male-sterile allele.
$ms^+$-=at least one dominant allele at the ms locus.
$ms^+$=normal allele at the ms locus on the chromosome.
ja=a recessive mutant juvenile-albino allele.
$ja^+$=normal allele at the ja locus on the chromosome.

Watermelon normally has eleven (11) pairs of chromosomes in the nucleus of each cell of the plant or seed thereof. A gene that governs fertility of male flowers, i.e., the production of pollen, exists at one site (or locus) in one pair of chromosomes out of the eleven pairs in each cell. This male fertility gene has a mutant form, known as the male-sterile (denoted by ms) gene, which is of interest for practicing the present invention. The male-sterile gene may exist at this locus on each chromosome of the chromosome pair. When the male-sterile gene exists on both chromosomes of the pair (homozygous), then that plant becomes incapable of producing pollen—a condition known as male sterility. Such a plant is known as a male-sterile plant. Thus, when the male-sterile ms gene is homozygous, then the male flowers of the watermelon plant are prevented from producing pollen. The normal allele $ms^+$ governs normal production of pollen.

However, if only one male-sterile gene exists on one chromosome and its partner gene on the other chromosome is a normal male-fertile gene, then the plant with this genotype will not suffer from the male sterility condition. In this case the mutant male-sterile gene is not expressed, because the expression of the mutant gene ms is masked by its allele, $ms^+$. The normal allele, $ms^+$, is said to be dominant, and the mutant allele, ms, is said to be recessive. Thus, the male-sterile gene of interest for practicing the present invention is a mutant recessive male-sterile gene.

On another pair of chromosomes in the eleven pairs in the watermelon plant (it might be remotely located on the same pair of chromosomes that carry the ms gene for that matter), there is a normal gene that enables the plant to produce normal cotyledons, leaves, foliage and fruit. Applicants have discovered that this normal "greening" gene has a mutant form, which they have named the juvenile-albino (ja) gene, that is of interest for practicing the present invention in watermelon. The juvenile-albino (ja) gene is the abnormal counterpart of the allele ($ja^+$) and prevents the normal greening of the plant. However, the juvenile albino (ja) gene only expresses itself in the watermelon plant when homozygous (present in both chromosomes in the pair), and thus is a recessive gene. Moreover, even when the ja gene is homozygous, the expression of the ja gene is regulated by the length of day. This mutant recessive ja gene, which is located on another chromosome (pair) of the eleven (11) pairs in watermelon (it might be on the same pair of chromosomes that carry the ms gene but remotely located from the ms gene), prevents the normal greening of the leaf/plant when days are short. Thus, the juvenile-albino gene is a conditional mutant gene because the ja gene only expresses itself fully when the plant is subjected to specified environmental conditions. In the case of this particular juvenile-albino gene, the triggering environmental condition is shortened daylength. Thus, the juvenile-albino gene of interest for practicing the present invention is a conditional, recessive, "slow greening" gene.

As known in the art, a plant "line" has been inbred for as many generations as necessary to "fix" chosen characteristics such as rind color, flesh color, fruit shape, disease resistance, etc. Seed companies maintain plant lines to produce seed that will grow into plants with these characteristics desired by the farmers and other growers who are the customers of the seed company. Seed companies also use two inbred lines to produce a desired hybrid line.

In accordance with the present invention, two very different recessive genes (ms and ja) that exist on entirely different chromosome sets (or on the same chromosome set at a remote site) and that when each gene is homozygous in the nuclei of a plant express two different physical (phenotypic) characteristics (male sterility and chlorosis of the leaves) in that plant, are introduced into the desirable plant variety or breeding line that thereafter is used as female parent to produce hybrid seed of a desired hybrid variety. This desirable plant variety or breeding line is a double recessive genic stock.

A preferred embodiment of the present invention will be described as it has been applied to a form of monoecious plant, and in particular the watermelon. However, the present invention also could be applied to other plant species, including non-monoecious species, provided a suitable male-sterile gene and a suitable marker gene are identified for such other plant species.

The suitable male-sterile gene has the following characteristics. First, the suitable male-sterile gene is stable. That is to say, despite varying environmental conditions including temperature, photoperiod and intensity, and water-stress in different years, seasons and locations, the ms mutant always expresses its male-sterile and female-fertile character. Second, the male-sterile character expressed by the suitable male-sterile gene, means that female flowers on male-sterile plants have the same color, shape and size as the female flowers on male-fertile plants. For an effective application of male sterility in hybrid seed production, it is critical that normal female fertility be retained in the male-sterile mutant. Third, the male-sterile character expressed by the suitable male-sterile gene, means that the sterile male flowers never produce pollen. Fourth, the male-sterile character expressed by the suitable male-sterile gene, means that breeding characteristics such as fruit set, fruit development, and fertility of male-sterile plants are the same as the male-fertile siblings within the original breeding line and other breeding lines of different genetic origin with ms gene introduced. Fifth, the male-sterile character expressed by the suitable male-sterile gene, means that the floral morphology and flower fertility of the heterozygous (ms$^+$ms) plants are identical to those of the homozygous (ms$^+$ms$^+$) plants in the different genetic backgrounds. Therefore, the heterozygous condition will not affect the fertility of the final hybrids resulting from the hybridization of male-sterile plants with the ms$^+$ms$^+$ plants as pollen parent.

The suitable marker gene has the following characteristics. First, the suitable marker mutant gene must be easy to recognize. Unlike the present invention, the Mohr et al method used an incompletely dominant seedling marker, and therefore the hybrid cannot be recognized until true leaves have matured using the Mohr et al method. Second, the suitable marker mutant gene expresses itself as early as seedling emergence and in the seed stage if possible. Third, the marker character expressed by the suitable marker mutant gene does not affect female fertility and fruit setting of the plant. The marker mutant is just as fertile and, ideally, sets as many fruit same as the wild-type. Fourth, ideally, the expression of the suitable marker mutant gene is conditional, i.e., its expression can be regulated by changing environmental conditions.

The following so-called "stock" protocol can be used to produce the double recessive genic stock that thereafter can be used in generating the desired marked genic male-sterile female parent stock for producing seed of a desired hybrid variety. The male flowers or flower parts (stamens) in this double recessive genic stock will be sterile. Watermelon has been chosen as the exemplary embodiment discussed below. Watermelon is a monoecious (separate male and female flowers) plant variety. Accordingly, each plant of the resulting double recessive genic watermelon stock, has male flowers and separate female flowers, and the male flowers will be sterile. However, in other embodiments of the present invention, the crops may have perfect flowers with both sex organs in the same flower.

The mutant recessive genes that are suitable genes to be used in the present invention have been chosen so that they do not have any adverse effects on seed productivity of the genic male-sterile line and the variety of hybrid plant that is desired. For example, the male-sterile gene (ms) and the juvenile-albino gene (ja) do not adversely affect the amount of seed produced by the female flowers, and so female fertility is maintained after introduction of the two genes into the desired inbred line. In addition, the male-sterile gene (ms) and the juvenile-albino gene (ja) do not adversely affect the amount of fruit (in this case watermelons) produced by the mature hybrid plants, and so the productivity of the hybrid plants is maintained when these two genes are used for producing the seed of the desired hybrid variety. Moreover, the presence of the two genes in the desired hybrid line has not adversely affected the vigor of the mature hybrid plants.

The particular features of the suitable mutant male-sterile gene (ms) for watermelon are as follows. Despite the varying environmental conditions including temperature, photo-period and intensity, and water-stress in different years, seasons and locations, the ms mutant always expresses its male-sterile and female-fertile character. In addition, the sterile male flowers never produce pollen. The development of male flowers is greatly affected by the mutation. The size of the fertile male flower bud increases greatly in seven (7) to ten (10) days before anthesis, whereas the size of sterile male flower remains relatively small during its development. The enlargement of the fertile male flower results from simultaneous growth of anthers, petals and sepals, but only petals and sepals grow in sterile male flowers. Before anthesis (shedding of pollen), sterile and fertile flowers are easily distinguished by pressing the flower bud between the fingers: the sterile flower buds collapse, but the fertile flower buds are firm. Size differences between sterile and fertile flowers depend on the plant vigor and age. When a fruit is developing on a watermelon plant, the development of sterile flower buds is inhibited. These buds become yellowish, the anthers become brown in color, and the flowers remain unopened. Male-sterile flowers on vigorous plants without fruit are larger and bloom like fertile male flowers. However, even on vigorous plants, the anthers and petals of sterile flowers are smaller than those of fertile one. If plant nutrition is near optimal, the petals of sterile flowers can reach the size of petals of fertile flowers. Though the relative size of petals is regulated by growing conditions, the anthers of sterile flowers are consistently smaller than anthers of fertile flowers. Moreover, female flowers on male-sterile plants have the same color, shape and size as the female flowers on male-fertile plants. Breeding characteristics such as fruit set, fruit development, and female fertility of male-sterile plants are the same as the male-fertile siblings within breeding lines of different genetic origin with ms gene introduced. Normal female fertility of a male-sterile mutant is critical for effective application of male sterility in hybrid seed production. Furthermore, the floral morphology and flower fertility of the heterozygous (ms$^+$ms) plants are identical to those of the homozygous (ms$^+$ms$^+$) plants in various genetic backgrounds. Complete dominance of the normal (ms$^+$) allele over the recessive ms allele is observed in all breeding lines with ms gene introduced. Therefore, the heterozygous condition will not affect the fertility of the final hybrids resulting from the hybridization of male-fertile (ms$^+$ms$^+$) plants as pollen parent.

The suitable marker gene has been chosen so that it is expressed as early as possible in the life of the plant. Ideally, the suitable marker would express itself in the seed, and some markers in crops other than watermelon do. However, one suitable marker gene for watermelon is the juvenile-albino gene (ja), which expresses itself as soon as the seed leaves (cotyledons) emerge from the soil, thereby allowing identification and segregation of desired plants from undesired plants at a relatively early stage (7 to 10 days normally) after the seeds are planted. When seedlings first emerge from the soil, cotyledons are yellowish to light cream, and gradually turn to greenish-yellow. The hypocotyl of the ja mutant is always pure white. In contrast, the wild-type hypocotyl is light green. When grown in spring/early summer in South Carolina, young leaves of the mutant are yellowish to white. As the plant develops, these albino leaves gradually become green, but the margins of the leaves remain white, resulting in a chimeric appearance to the mature leaves. Shoot tips, tendrils, petioles, stems, and flower petals of the mutant are white to light cream with a slight hint of green. Pollen grains from albino flowers are colorless, but are viable. The stigmas are orange, apparently lacking chlorophyll. The ovary color varies from light green to pure white. Some portions of the fruit rind are unevenly yellow, showing that rind color of mature fruit is also affected by the ja gene. In addition to these chlorophyll differences, the flower petals of the ja mutant are considerably smaller than those of the wild-type. The petals of some flowers are not large enough to cover the stigma or anthers. Importantly, female fertility and fruit setting of the mutant is same as that of the wild-type. Moreover, the ja gene does not affect the flesh color of the fruit. Growth of the ja mutant in early spring is severely impaired. The ja seedlings grow very slowly when they are planted in February and March in the greenhouse, and many of them die when it is cloudy and/or they receive too much water. Growth of the ja mutant plants improves as the season progresses, and in the summer they grow comparably to the wild-type. Branches produced in the ja mutant from the main shoots in the summer are almost normal green. Flowers produced by these branches are normal in color and size. Modification of ja expression in different seasons has been observed in all genetic stocks where ja was introduced.

In an alternative embodiment for watermelon, the marker gene can be the delayed-green (dg), a recessive virescent, instead of juvenile-albino.

Broadly speaking, the stock protocol, which also can be called the donor protocol because it involves development of a donor line for the double recessive genotype, involves developing a line with the desired male-sterile gene and the desired marker gene to produce the double recessive genetic stock, and maintaining this double recessive genetic stock. The stock protocol can begin with a plant homozygous for the male-sterile gene and pollinating this plant with a pollen from a plant with the marker gene. Once the desired genes have been identified, the manner of developing a line with such genes is well understood and therefore need not be described herein in any detail. In the illustrative preferred embodiment of the present invention, the two recessive genes for producing monoecious watermelon hybrid varieties, are the recessive mutant male-sterile gene (ms) and the conditional, recessive "slow greening" mutant, juvenile-albino gene (ja). The plant with the desired male-sterile gene can be represented as msmsja$^+$ja$^+$. The inbred line with the desired marker gene, in this case the juvenile-albino gene (ja), can be represented as ms$^+$ms$^+$jaja.

Broadly speaking, once the two breeding lines (one homozygous for the suitable recessive male-sterile gene and the other homozygous for the suitable recessive marker gene) have been established, the next step in the stock protocol involves crossing male-sterile plants of the chosen genic is male-sterile line with male-fertile plants of the chosen marker line (having the desired marker genotype) to obtain the first generation hybrid ($F_1$) of this cross. In the illustrative watermelon example, this step begins by inter-planting the genic male-sterile inbred female parent line (consisting of 50% ms$^+$msja$^+$ja$^+$, which is fertile, and 50% msmsja$^+$ja$^+$, which is sterile) with the inbred marker male parent line (ms$^+$ms$^+$jaja). Thus seed of the genic male-sterile parent line is planted in one row, and seed of the marker pollen line is planted in an adjacent row. The normal green plants, if any, in the marker line are eliminated at the seedling stage, thereby leaving only the desired marked plants to become the male parent of the desired cross-pollination. Then, just before the plants attain the flowering stage, and when male-fertile plants can be recognized, the male-fertile plants in the genic male-sterile line are removed. At this point in the stock protocol, identification using the marker and male sterility have permitted elimination of all of the plants except plants having the desired genotypes. The remaining plants are allowed to mature. Because the plants expressing the male-sterile genotype have male flowers that are incapable of producing pollen, they become the female parent in the following cross-pollination step.

Cross-pollination between the remaining mature plants (genic male-sterile plants and suitable marker plants) is allowed to proceed naturally by bees. This natural cross-pollination eliminates the need for time-consuming and expensive hand pollination. The plants of the desired inbred marker line (denoted by ms$^+$ms$^+$jaja) have fertile male flowers, which supply pollen to fertilize the female flowers of the female parent (the male-sterile plants denoted by msmsja$^+$ja$^+$). The desired result of this natural cross-pollination step is the first generation ($F_1$) filial progeny. To obtain the first generation ($F_1$) filial progeny, the seed are harvested only from the fruit of the plants in the male-sterile line. This seed of the first generation progeny ($F_1$) of this initial natural cross has a genotype that can be represented by the notation: ms$^+$msja$^+$ja.

In the next step of the stock protocol, the first generation progeny (ms$^+$msja$^+$ja) are self-pollinated to obtain the second generation filial progeny ($F_2$). This step begins by planting the first generation seed. Because both the ms gene and the ja gene are recessive, the first generation ($F_1$) offspring of the cross between the two lines are male-fertile and exhibit the normal green coloration. When the plants are mature, the pollen from the male flowers of each plant is applied to the female flowers of the same plant. Desirably, only the best specimens are chosen for this self-pollination step, which is performed by hand and can be represented as follows: ms$^+$msja$^+$ja×ms$^+$msja$^+$ja. The following chart presents the assortment of gametes involved in this self-pollination and the phenotypes obtained from this self-pollination:

| Gametes | ms⁺ja⁺ | ms⁺ja | msja⁺ | msja |
|---|---|---|---|---|
| ms⁺ja⁺ | normal | normal | normal | normal |
| ms⁺ja | normal | juvenile albino | normal | juvenile albino |
| msja⁺ | normal | normal | male sterile | male sterile |
| msja | normal | juvenile albino | male sterile | male sterile juv. albino |

Expressed in the shorthand notation, the seeds harvested from this self-pollination step constitute a second filial generation ($F_2$) with the following ratio of progeny: $9ms^+$–$ja^+$_:$3ms^+$–$jaja$:$3msmsja^+$–:$1msmsjaja$. Thus, about one of every sixteen (1/16) of the second filial generation ($F_2$) will be male-sterile, juvenile-albino (msmsjaja) individuals that in many ways resemble the desired individuals that will form the double recessive genetic stock that is the desired result of the stock protocol. The seed for producing $F_2$ progeny is harvested from all of the self-pollinated (selfed) $F_1$ plants.

In the next step of the stock protocol, at least one selected marked male-sterile $F_2$ plant is cross-pollinated by hand with a selected marked male-fertile $F_2$ sibling to produce the third generation filial offspring ($F_3$). As noted, this next step involves selecting from among the $F_2$ progeny, and the selection involves eliminating unmarked $F_2$ progeny. The selection occurs as soon as possible. Some varieties will enable selection to be made as soon as the $F_2$ seed are harvested. However, other varieties such as the watermelon of the example, will require the $F_2$ seed to be planted before the marked characteristic becomes expressed sufficiently for identification. In this latter case, this next step in the stock protocol begins by planting the seed for the $F_2$ progeny. As the seedlings emerge, the normal green plants are eliminated. As can be seen from reference to the above chart, this will leave only about 25% of the planted $F_2$ progeny. Moreover, of these remaining 25% of the planted $F_2$ progeny, three out of four (3/4) plants will be male-fertile marked plants. The remaining one out of four (1/4) plants will be male-sterile marked plants. Thus, the remaining second filial generation ($F_2$) plants will be marked male-fertile (ms⁺–jaja) plants and marked male-sterile (msmsjaja) plants in a ratio of about three of the former to one of the latter.

Just before the marked second generation ($F_2$) plants attain the flowering stage, the male-fertile plants and the male-sterile plants are identified by examining the male flowers. As noted above in describing the ms gene for watermelon, the firm robust male flowers are fertile, and the smaller flaccid male flowers are sterile. At this stage in the stock protocol, identification using the marker and male sterility has permitted elimination of all of the plants except plants having the desired recessive marker genotype. Since the plants having the male-sterile genotype have male flowers that are incapable of producing pollen, they become the female parent in the following cross-pollination step of the chosen second generation ($F_2$) siblings.

In the next step of the stock protocol, the best specimen among the male-sterile plants and the best specimen among the male-fertile plants are selected as the two siblings for cross-pollination. These chosen second generation ($F_2$) siblings are cross-pollinated by hand to yield the third filial generation ($F_3$). This selected sibling-cross step (sib-cross) can be performed with more than one pair of specimens if desired. Cross-pollinating the selected second generation ($F_2$) siblings results in a third filial generation ($F_3$). The seeds for producing the third filial generation ($F_3$) progeny are harvested only from the fruit of the marked male-sterile plant (or plants). As such, only two types of sib-crosses will be reflected in the seed harvested from the marked male-sterile plant (or plants).

Each of the two possible sib-crosses results in third generation ($F_3$) progeny of different genotype populations. The undesired (for purposes of the present invention) sib-cross produces third filial generation ($F_3$) offspring that are all (100%) marked and male-fertile. This undesired sib-cross and its resulting third filial generation ($F_3$) genotype population can be represented by the following notation:

msmsjaja×ms⁺ms⁺jaja→ms⁺msjaja ($F_3$ offspring)

The desired (for purposes of the present invention) sib-cross produces third filial generation ($F_3$) offspring that are half (50%) marked and male-fertile and half (50%) marked and male-sterile. This desired sib-cross and its resulting third filial generation ($F_3$) genotype population can be represented by the following notation:

msmsjaja×ms⁺msjaja→1msmsjaja:1ms⁺msjaja

In the next step of the stock protocol, the third filial generation ($F_3$) seeds are harvested from each individual fruit of the selected sib-crossed male-sterile second filial generation ($F_2$) plants. The seed from each fruit is kept segregated in a separate lot of seed.

In the next step of the stock protocol, each lot of the third filial generation ($F_3$) seed, which was taken from an individual fruit from a male-sterile plant, is planted in its own separate plot and allowed to grow out. Just before the plants in each plot reach flowering stage, the plants in each separate plot are inspected to determine whether they have the genotype population that is characteristic of the desired sib-cross or the undesired sib-cross. The inspection focuses on the male flowers to distinguish the fertile male flowers from the sterile flowers. Then the plots with the genotype population from the undesired sib-cross are no longer of concern to the stock protocol and can be abandoned.

In the next step of the stock protocol, the plots with the genotype population from the desired sib-cross are open-pollinated in isolation to produce the fourth generation ($F_4$) progeny. This open-pollination step can be represented by the notation: msmsjaja×ms⁺msjaja→1msmsjaja:1ms⁺msjaja. Seeds are harvested only from the male-sterile msmsjaja plant(s). The result of this open-pollination of the desired sib-cross becomes itself the desired sib-cross. Accordingly, each fruit from plants in the desired sib-cross plots bears the fourth filial generation ($F_4$) progeny and therefore contains seed that will grow a genotype population in which half (50%) of the plants will have the marked and male-fertile genotype (ms⁺msjaja) and the other half (50%) of the plants will have the marked and male-sterile genotype (msmsjaja). Thus, half of the fourth filial generation ($F_4$) progeny seed will produce the desired double recessive genic stock, which has the genotype represented by the msmsjaja notation.

In the final step of the stock protocol, the fourth filial generation ($F_4$) progeny seed is harvested from the fruit of the male-sterile plants. When this harvested $F_4$ progeny seed is planted and allowed to grow out, and the marked male-fertile plants are eliminated, the remaining marked male-sterile plants become the double recessive genetic stock line that can be used in the transfer protocol described below.

Moreover, the $F_4$ progeny seed can be continually maintained, i.e., replenished, by planting it in isolation plots, open-pollinating the plants, and harvesting the seed only from the fruit of the male-sterile plants. Plants grown from this harvested seed will have a genotype population consisting of half (50%) marked and male-fertile plants and half (50%) marked and male-sterile plants. When this harvested seed is planted and allowed to grow out, the grower can eliminate the marked male-fertile plants. Then the remaining marked male-sterile plants become the double recessive genetic stock line that can be used in the transfer protocol described below.

Applicants presently contemplate that exploitation of the present invention would involve providing commercial seed companies with hybrid seed and/or a better method for producing hybrid seed for the hybrid plant varieties that are most desired by the seed company's customers. The present invention would be used to improve the inbred lines maintained by the seed companies. This is done by transferring the desired two independently assorting genes (ms and ja for watermelon for example) into the genetic makeup (genotype) of the inbred line maintained and used by the seed company to produce the seed of hybrid varieties desired by farmers and other growers. Thus, to use the hybrid seed production method of the present invention to produce seed of a certain kind of watermelon (variety), it is first necessary to use a so-called "transfer" protocol to transfer the above two independently assorting genes (ms and ja) into the genetic makeup (genotype) of the desired inbred line. The transfer protocol described below requires about three (3) years (assuming 2 to 3 crops per year) of hand labor to make the specific crosses and select the specific phenotypes that are needed to produce the desired double recessive genic (msmsjaja) inbred line.

The following so-called "transfer" protocol can be used to transfer the above two independently assorting genes (ms and ja) into the genetic makeup (genotype) of the desired inbred line to produce the marked genic male-sterile female parent stock that thereafter can be used by a seed company as the female parent line (seed parent line) for producing hybrid seed to be sold to the customers of the seed company. The transfer protocol can be used for a monoecious plant species/variety, which by definition means that each plant has male flowers and separate female flowers. The transfer protocol also can be used for a species/variety that is non-monoecious. The transfer protocol begins with the double recessive genic stock, which can be obtained in the manner described above using the stock protocol.

Applicants have deposited a sample of viable seed from the double recessive genic stock containing the male-sterile and juvenile-albino genes (ms and ja) for watermelon in the American Type Culture Collection, 12301 Parklawn Drive, Rockville, Md. 20852 on Sep. 19, 1996 and have been assigned ATCC Designation No. 97723, which seed deposit is incorporated herein by this reference. This seed deposit has the following identification at ATCC: Male sterile Juvenile Albino Watermelon Seed 93JMSB1-1 (msmsjaja× Msmsjaja). Applicants also have deposited a sample of viable seed from the double recessive genic stock containing the male-sterile and delayed green genes (ms and dg) for watermelon in the American Type Culture Collection and have been assigned ATCC Designation No. 97706, which seed deposit is incorporated herein by this reference. This seed deposit has the following identification at ATCC: Male sterile Delayed Green Watermelon Seed, MSDG-1 (msmsdgdg×Msmsdgdg).

Broadly speaking, the first step in the transfer protocol involves crossing plants of the desired inbred line (the female parent of the desired hybrid variety) with the double recessive genic stock (having the genotype including the two recessive genes). In the exemplary embodiment of the present invention, the two recessive genes for producing watermelon hybrid varieties, are the recessive mutant male-sterile gene (ms) and the marker gene. In the case of the exemplary embodiment of the present invention, the marker gene for producing watermelon hybrid varieties, is the conditional, recessive virescent mutant, juvenile-albino gene (ja).

The transfer protocol begins by choosing one of the two inbred lines used to produce the desired hybrid, as the candidate for receiving the male-sterile gene and the marker gene. The inbred line will be the one that, in the breeder's experience, has proven to be the most suitable seed parent (female) of a hybrid variety because of such factors as its disease resistance, earliness, vigor, desired plant shape/pattern, high seed yield, and desired seed characteristics.

The next step in the transfer protocol calls for interplanting the marked genetic male-sterile female parent line with the normal seed parent line of the desired hybrid variety. This involves planting seed of the double recessive genetic stock in one row and planting seed of the chosen desired inbred line in an adjacent row. If any normal green plants emerge in the rows of planted double recessive genic stock, these normal green plants are eliminated at the seedling stage, thereby leaving only the virescent plants in the rows of double recessive genic stock. Moreover, as described above, the seed produced using the stock protocol contains half double recessive genic stock (msmsjaja) and half marked male-fertile stock (ms$^+$msjaja). Thus, in the next step in the transfer protocol, just before the plants attain the flowering stage, the male-fertile plants are removed from the plant rows containing the double recessive genetic stock line. At this stage in the transfer protocol, identification using the marker and male sterility have permitted elimination of all of the plants from the rows of double recessive genic stock, except plants having the desired double recessive genotype (msmsjaja), i.e., marked plants with sterile male flowers. Since the plants having the desired double recessive genotype are male-sterile, they have male flowers that are incapable of producing pollen and thus become the female parent in the following cross-pollination step.

In the next step of the transfer protocol, cross-pollination between the rows of plants containing the double recessive genetic stock (msmsjaja) and the rows of plants containing the desired inbred line (denoted by ms$^+$ms$^+$ja$^+$ja$^+$) is allowed to proceed naturally by bees. This natural cross-pollination eliminates the need for time-consuming and expensive hand pollination. The plants of the desired inbred variety have fertile male flowers, which supply pollen to fertilize the female flowers of the female parent (the double recessive genetic stock). The result of this natural cross-pollination step is the first generation ($F_1$) progeny.

In the next step of the transfer protocol, the fruit are harvested from the plants in the female parent line (double recessive genetic stock). The seed harvested from this fruit constitute the first generation filial offspring ($F_1$) of this cross-pollination. Using the shorthand notation described above, the desired result of this cross-pollination step can be summarized as follows: msmsjaja(female)×ms$^+$ms$^+$ja$^+$ja$^+$ (male)→ms$^+$msja$^+$ja($F_1$)

Because both the ms gene and the ja gene are recessive, the first generation ($F_1$) offspring (ms$^+$msja$^+$ja) are male-fertile and exhibit the normal green coloration.

Broadly speaking, in the next step of the transfer protocol, the first generation filial offspring ($F_1$) of the cross-pollination are self-pollinated by hand pollination (or open pollination in an isolation plot) to produce the second filial generation of progeny (denoted by $F_2$). This self-pollination step begins by planting the first generation ($F_1$) seed harvested from the fruit produced by the male-sterile plants after the cross. This step of the transfer protocol requires the marked members of the first filial generation ($F_1$) to be eliminated from the field. As the seeds germinate and reach the cotyledon or seedling stage, the seedlings that exhibit the marker (the white coloration produced by the ja gene) are eliminated from the stand, leaving only normal green seedlings to become mature plants. These mature normal green and male-fertile first generation filial offspring of the cross-pollination are self-pollinated. In each normal green and male-fertile plant, the pollen from the male flowers in the plant is transferred by hand to the female flowers of the same male-fertile plant. This self-pollination step results in a second filial generation ($F_2$) with the following ratio of progeny:

$ms^+msja^+ja(selfed) \rightarrow 9ms^+-ja^+-:3ms^+-jaja:3msmsja^+-:1msmsjaja$

The following chart presents the assortment of gametes involved in this self-pollination and the phenotypes obtained from this self-pollination:

| Gametes | $ms^+ja^+$ | $ms^+ja$ | $msja^+$ | msja |
|---|---|---|---|---|
| $ms^+ja^+$ | normal | normal | normal | normal |
| $ms^+ja$ | normal | juvenile albino | normal | juvenile albino |
| $msja^+$ | normal | normal | male sterile | male sterile |
| msja | normal | juvenile albino | male sterile | male sterile juv. albino |

Thus, about one of every sixteen (1/16) of the second filial generation ($F_2$) progeny will be male-sterile, juvenile-albino (msmsjaja) individuals.

In the next step of the transfer protocol, the very best second filial generation individual (that which most resembles the desired inbred line) that is male-sterile, juvenile-albino is cross-pollinated back ("backcrossed") to the desired inbred line. This is accomplished by interplanting seed (or transplanting the jaja seedlings) of the second filial generation of progeny ($F_2$) with seed of the desired inbred line ($ms^+ms^+ja^+ja^+$). The seed of the second filial generation of progeny ($F_2$) are preferably planted three (3) seeds per hill or cell (of a flat) in alternating rows. The desired inbred seed can be planted one (1) or two (2) seeds per hill in rows disposed between the rows of $F_2$ progeny. As the seeds germinate and reach the cotyledon or seedling stage, the $F_2$ progeny seedlings that fail to exhibit the marker (in this embodiment, the white coloration produced by the ja gene) are eliminated from the stand, leaving only marked $F_2$ progeny with one of the following genotypes: $ms^+ms^+jaja$; $ms^+msjaja$; and msmsjaja. These marked $F_2$ progeny are further selected just before the flowering stage to eliminate all male-fertile individuals. The remaining male-sterile marked $F_2$ progeny (msmsjaja) are naturally pollinated by the pollen from the desired inbred line. The desired result of the backcross can be summarized by the following notation:

$msms\ jaja \times ms^+ms^+\ ja^+ja^+ \rightarrow ms^+ms\ ja^+ja$

In the next step of the transfer protocol, the fruit on the male-sterile marked $F_2$ progeny are inspected and selected for those fruit that most resemble the fruit of the desired inbred line. The seed harvested from the selected fruit of the male-sterile, juvenile-albino plants become the seed of the first generation backcross progeny ($BC_1$). The first generation backcross progeny ($BC_1$) will be more like the desired inbred parent line but will also contain the essential genes (ms ja) for production of the desired hybrid seed.

Broadly speaking, the transfer protocol proceeds by repeating the following successive steps. First, each generation of backcross progeny ($BC_n$) is self-pollinated to obtain subsequent filial generation progeny. Then the male-sterile, juvenile-albino individuals of the subsequent filial generation progeny are selected for the individuals that most resemble the desired inbred line and these selected individuals of the subsequent filial generation progeny are backcross-pollinated with the desired inbred line. These successive steps of self-pollination of each successive backcross progeny ($BC_n$) and backcross-pollination of successive selected filial generation progeny are repeated until the derived line is uniformly like the desired inbred line except for the expression of the male-sterile gene and the marker gene when the following cross is made:

$msms\ jaja \times ms^+ms\ jaja \rightarrow 1\ msms\ jaja:1\ ms^+ms\ jaja$

These repetitions may need to continue through about six (6) to eight (8) backcross generations in order to ensure that the derived marked male-sterile line is not segregating for important economic characters such as yield, sugar, rind color, earliness, etc. At the conclusion of these six to eight repetitions, the derived line becomes the marked genic male-sterile female parent stock, whose fruit types are identical to the desired inbred line except for the juvenile-albino trait and the one-to-one (1:1) assortment of (male-sterile)-to -(male-fertile). The seed produced by and harvested from the male-sterile plants of the derived line, when grown out, becomes the seed parent needed to produce the hybrid seed.

The double recessive marked genic male-sterile stock can be maintained by the seed company by continually saving seed from the male-sterile plants in the derived line produced in the last step of the transfer protocol. Plants 10-o from these seed will always segregate (assort into) male-sterile and male-fertile plants in a one-to-one (1:1) ratio, as summarized in the notation above. Any off-type resulting from out-crossing or mixing in the marked genic male-sterile line can be detected at the seedling stage by the absence of the marker trait.

Note that in a further alternative embodiment, the diploid marked male-sterile line can be used to produce tetraploid marked genic male-sterile line, which in turn can be used for making triploid hybrid seed. This is briefly, described for watermelon as follows. After the transfer protocol has been completed, the following genotypes are obtained and segregate in the following way:

1 msmsjaja×1 $ms^+$msjaja

These two genotypes can be used to produce tetraploid derivatives, which can be used as a tetraploid marked genic male sterile line as female parent for triploid hybrid seed production. After the tetraploid marked genic male sterile line is obtained, the male sterile female is used like the diploid male sterile female in seed production. Briefly, the tetraploids are generated in the following manner. First, the seedlings of both genotypes are grown. Then, treat the apex of the young seedling with 0.2%–0.4% colchicine. Thirdly, identify the tetraploids (4×) by leaf, plant morphology, and finally by seed characters or even chromosome counting. Fourthly, sibcross male sterile and male fertile tetraploid plants to obtain cross-pollinated progeny. Harvest seed from cross-pollinated male sterile plants at fruit maturity. Then, grow out the cross-pollinated progeny. Sibcross individual male sterile and male fertile tetraploid plants in the cross-pollinated progeny. Save seed separately from each cross. Then, grow out all the cross progenies. From these progenies, look for progenies that are segregating in a one-to-one (1:1) ratio with respect to male sterility. Eliminate all other progenies. Allow open pollination of these remaining progeny and harvest seed only from the male sterile plants. These seeds will produce the tetraploid marked male sterile line that has a population consisting of one (1) msmsmsmsjajajaja individual for every one (1) msmsmsms⁺jajajaja individual.

Finally, the commercial breeder can prepare the seed parent for hybridization by planting the marked genic male-sterile stock (the 1:1 male-sterile:male-fertile segregating line) in the field; eliminating the male-fertile plants (based on the morphology of the male flower bud, which can be examined at the early flowering stage); and allowing bee pollination from the chosen pollen parent line or variety with the genotype ms⁺ms⁺ja⁺ja⁺. The pollen parent should be planted in a ratio of one (1) row to from two (2) to four (4) rows of plants from the male-sterile parent line.

Commercial hybrid seed will be harvested only from the male-sterile plants. If male-fertile plants have been eliminated completely from the seed parent row, the seed from the fruit of the pollen parent can be saved for future pollinations.

The hybrid seed can be planted by the farmer or grower at a relatively high rate, i.e., two (2) seeds per hill or cell (of a flat), and the marked inbreds, if any, are removed at the cotyledon or seedling stage (or later). Removal of inbred plants can be accomplished at the early seedling stage by the transplant greenhouse operator or growers, and thus before fruiting. However, if inbreds are not removed, fruit are readily discernible as marked and undersized and can be left in the field.

The preferred embodiment of the present invention described above applies to a form of diploid watermelon. However, an alternative embodiment of the present invention also can be applied to produce tetraploid lines for producing triploid "seedless" watermelon seed. The chromosome number of the diploid seed parent is doubled to produce a tetraploid marked, male-sterile line.

Moreover, applicants believe that the present invention can be practiced in other cucurbit crops than watermelon. Applicants believe that different male-sterile genes and different marker genes can be used in combination in the stock protocol to produce the double recessive genetic stock that can be used in the transfer protocol. In this regard, applicants present several combinations of suitable male-sterile and marker genes for melon, several combinations of suitable male-sterile and marker genes for cucumber, several combinations of suitable male-sterile and marker genes for squash, several combinations of suitable male-sterile and marker genes for beans, several combinations of suitable male-sterile and marker genes for edible soybeans.

For melon, any one of the following male-sterile genes (ms-1 and ms-5) can be combined with any one of the following marker genes (fe; h; r; v; yv; and yv-2) to produce the double recessive genetic stock needed to practice the transfer protocol of the present invention. The male sterile-1 (ms-1) gene is known for melon and reported in Bohn, G. W. and T. W. Whitaker, "A Gene for Male Sterility in Muskmelon (*Cucumis melo* L.)," *Proc. Ameri. Soc. Hort. Sci.* 53:309–314 (1949), which is incorporated herein by this reference. The male sterile-5 (ms-5) gene is known for melon and reported in Lecouviour, M., M. Pitrat and G. Risser, "A Fifth Gene for Male Sterility in *Cucumis melo*," *Cucurbit Genetics Coop. Rept.* 13:34–35 (1990), which is incorporated herein by this reference. The iron inefficient mutant (fe) gene is a marker gene that is known for melon and reported in Nugent, P. E. and H. S. Bhella, "A New Chlorotic Mutant of Muskmelon," *HortScience* 23:379–381 (1988), which is incorporated herein by this reference. The halo cotyledons mutant (h) gene is a marker gene that is known for melon and reported in Nugent, P. E. and J. C. Hoffman, "Inheritance of the Halo Cotyledon Mutant in Muskmelon," *J. Hered.* 65:315–316 (1974), which is incorporated herein by this reference. The red stem mutant (r) gene is a marker gene that is known for melon and reported in McCreight, J. D. and G. W. Bohn, "Descriptions, Genetics and Independent Assortment of Red Stem and Pale in Muskmelon (*Cucumis melo* L.)," *J. Amer. Soc. Hort. Sci.* 104:721–723 (1979), which is incorporated herein by this reference. The virescent mutant (v) gene is a marker gene that is known for melon and reported in Hoffman, J. C. and P. E. Nugent, "Inheritance of a Virescent Mutant of Muskmelon," *J. Hered.* 64:311–312 (1973), which is incorporated herein by this reference. The yellow virescent mutant (yv) gene is a marker gene that is known for melon and reported in Zink, F. W., "Linkage of Virescent Foliage and Plant Habit in Muskmelon," *J. Amer. Soc. Hort. Sci.* 102:613–615 (1977), which is incorporated herein by this reference. The yellow virescent-2 mutant (yv-2) gene is a marker gene that is known for melon and reported in Pitrat, M. G. Risser, C. Ferriere, C. Olivier and M. Riccard, "Two Virescent Mutants in Melon (*Cucumis melo*)," *Cucurbit Genetics Coop. Rept.* 14:45 (1991), which is incorporated herein by this reference.

For cucumber, the following male-sterile gene (ms-2) can be combined with any one of the following marker genes (al; lg-1; lg-2; ls; and ys) to produce the double recessive genetic stock needed to practice the transfer protocol of the present invention. The male sterile-2 (ms-2) gene is known for cucumber and reported in Pierce, L. K. and T. C. Webner, "Review of Genes and Linkage Group in Cucumber," *Hort-Science* 25:605–615 (1990), which is incorporated herein by this reference. The albino cotyledons mutant (al) gene is a marker gene that is known for cucumber and reported in Iida, S. and E. Amano, "Mutants induced by pollen irradiation in cucumber," *Cucurbit Genetics Coop. Rept.* 14:32–33 (1991), which is incorporated herein by this reference. The light green cotyledons-1 mutant (lg-1) gene is a marker gene that is known for cucumber and reported in Iida, S. and E. Amano, "Mutants induced by pollen irradiation in cucumber," *Cucurbit Genetics Coop. Rept.* 14:32–33 (1991). The light green cotyledons-2 mutant (lg-2) gene is a marker gene that is known for cucumber and reported in Iida, S. and E. Amano, "Mutants induced by pollen irradiation in cucumber," *Cucurbit Genetics Coop. Rept.* 14:32–33 (1991). The light sensitive mutant (ls) gene is a marker gene that is known for cucumber and reported in Whelan, E.D.P., "Inheritance of a Radiation-induced Light Sensitive Mutant of Cucumber," *J. Amer. Soc. Sci.* 97:765–767 (1972), which is incorporated herein by this reference. The yellow stem mutant (ys) gene is a marker gene that is known for cucumber and reported in Rucinska, M., K. Niemirowicz-Szczytt and A. Korzeniewska, "A Cucumber (*Cucumis sativus* L.) Mutant with Yellow Stem and Leaf Petioles," *Cucurbit Genetics Coop. Rept.* 14:8–9 (1991), which is incorporated herein by this reference.

For squash, any one of the following male-sterile genes (ms-1 and ms-2) can be combined with the following marker gene (v) to produce the double recessive genetic stock needed to practice the transfer protocol of the present invention. The male sterile-1 (ms-1) gene is known for squash and reported in Eisa, H. M. and H. M. Munger, "Male Sterility in *Cucurbita pepo*," *Proc. Amer. Soc. Hort. Sci.* 92:473–479 (1986), which is incorporated herein by this reference. The male sterile-2 (ms-2) gene is known for squash and reported in Eisa, H. M. and H. M. Munger, "Male Sterility in *Cucurbita pepo*," *Proc. Amer. Soc. Hort. Sci.* 92:473–479 (1986), which is incorporated herein by this reference. The virescent mutant (v) gene is a marker gene that is known for squash and reported in Hutto, M. G. and R. W. Robison, "Gene List for Cucurbita spp.," *Cucurbit Genetics Coop. Rept.* 15:102–109 (1992), which is incorporated herein by this reference.

For beans, the following male-sterile gene (ia) can be combined with any of the following marker genes (pal; $vir_f$, $ps_1$) to produce the double recessive genetic stock needed to practice the transfer protocol of the present invention. The indehiscent anther gene (ia) is a recessive gene that conditions male-sterility. The recessive indehiscent anther gene (ia) is known for bean and reported in Wyatt, J. E., "An Indehiscent Anther Mutant in the Common Bean," *Journal American Society of Horticultural Science*, Vol. 109, No. 4, pp 484–487 (1984), which is incorporated herein by this reference. The pale green recessive marker ($ps_1$) is known for bean and reported in Wyatt, J. E., *J. Heredity* 72(3); 218–219 (1981), which is incorporated herein by this reference. The mutant homozygous for $pa_1$ is known for bean and reported in Wyatt, J. E., *J. Heredity* 72(3); 218–219 (1981), which is incorporated herein by this reference. The $pa_1$ gene was light sensitive and therefore not as productive as a normal plant. However, it could be exploited as a marker gene in the present invention by shading the plant during line development and growing the hybrids, contaminated with inbreds, in full sun to minimize the effect of the inbreds. The virescent gene $vir_f$ is known for bean and reported in Grafton, K. F., Wyatt, J. E. and Welser, G. C., "Genetics of a Virescent Foliage Mutant in Beans," *J. Heredity*, 74(5); 385 (1983), which is incorporated herein by this reference. Like the pal gene, the $vir_f$ gene is also environmentally sensitive. However, zo this $vir_f$ marker could also be environmentally manipulated to expedite line development and maximize hybrid seed production.

For edible soybeans, any one of the following six male-sterile genes (ms-1; ms-2; ms-3; ms-4; ms-5; and ms-6) can be combined with the following marker gene ($y_{12}$) to produce the double recessive genetic stock needed to practice the transfer protocol of the present invention. The six male-sterile, female-fertile genes are known for edible soybean and reported in R. G. Palmer, M. C. Albertson, H. T. Horner and H. Skorupska, "Male Sterility in Soybean and Maize: Development Comparisons," *The Nucleus* 35:1–18 (1992), which is hereby incorporated herein by this reference. A suitable recessive seed/seedling marker is $y_{12}$, which is known for edible soybean and reported in Thomas M. Davis, Jeffrey D. Ehlers and Yun-Tsu Kiang, "Early Identification of Chlorophyll Deficiency Heterozygotes in Large Seeded Legumes," *J. Heredity*, 77(6); 475–476 (1986). The $y_{12}$ gene exhibits white-fringed trifoliate leaves at the seedling stage and normal leaves thereafter.

While a preferred embodiment of the invention has been described using specific terms, such description is for illustrative purposes only, and it is to be understood that changes and variations may be made without departing from the spirit or scope of the following claims.

What is claimed is:

1. A method of producing seed for commercial production of a desired cucurbit hybrid plant variety, comprising the steps of:

identifying a first cucurbit plant line with a suitable male-sterile gene;

identifying a second cucurbit plant line with a suitable marker gene, said marker gene being disposed with respect to said male-sterile gene in one of the following two relative dispositions, the first of said relative dispositions being on separate chromosomes and the second of said relative dispositions being on the same pair of chromosomes such that said male-sterile gene and said marker gene independently segregate;

crossing sufficient generations of progeny of said two lines to produce a genetic stock which is double recessive for said male-sterile and marker genes;

crossing said double recessive as a female parent with a suitable male parent; and harvesting hybrid seed from the female parent.

2. A method as in claim 1, further comprising the step of maintaining said double recessive genetic stock.

3. A method as in claim 1, further comprising the step of performing a transfer protocol that uses said double recessive genetic stock to introduce said male-sterile gene and said marker gene into a candidate of the female parent of a desired hybrid variety and produces a marked genetic male-sterile female parent line, said female parent line homozygous for said marker gene and heterozygous for said male-sterile gene.

4. A method as in claim 3, further comprising the step of crossing said double recessive genetic stock and the candidate of the female parent of the desired hybrid variety.

5. A method of producing seed for commercial production of a desired cucurbit hybrid plant variety, comprising the steps of:

performing in a cucurbit hybrid plant variety a transfer protocol that introduces by sexual reproduction a male-sterile recessive genetic mutant gene and a recessive marker gene, said marker gene being originally disposed with respect to said male-sterile gene in one of the following two relative dispositions, the first of said relative dispositions being on separate chromosomes and the second of said relative dispositions being on the same pair of chromosomes such that said male-sterile gene and said marker gene independently segregate;

said marker gene expressing itself as an identifiable characteristic in a seedling, into a candidate of the female parent of the desired hybrid variety and back-crossing and selfing sufficient generations of progeny to produce a marked genetic male-sterile female parent line crossing said marked genetic male-sterile female parent line with a suitable male parent; and harvesting hybrid seed from the female parent.

6. A method as in claim 5, wherein the seed used in said transfer protocol for introducing said male-sterile recessive genetic mutant gene and said marker gene, has a one to one ratio of male-sterile to male-fertile.

7. A method as in claim 5, wherein said transfer protocol comprises the steps of:

interplanting marked genic male-sterile plants with the female parent of the desired hybrid variety;

identifying and eliminating unmarked plant members from among the marked genetic male-sterile female parent plants at the seedling stage;

identifying and eliminating male-fertile plant members from among the marked genetic male-sterile female parent plants just before the flowering stage;

naturally cross-pollinating said female parent of the desired hybrid variety with said marked male-sterile plants remaining from said marked genic male-sterile plants; and when fruit are mature, only harvest the seed from said marked male-sterile plants, said seed being first generation cross seed.

8. A method as in claim 7, further comprising the steps of:

self-pollinating plants grown from said first generation cross seed to produce second filial generation progeny.

9. A method as in claim 8, wherein said self-pollination step further comprises the steps of:
   planting said first generation cross seed;
   identifying and eliminating the marked plant members from said first generation cross plants at the seedling stage;
   self-pollinating said remaining male-fertile plant members to produce seed of the second filial generation; and
   when fruit are mature, harvest the seed from at least one of the individual plants deemed desirable for propagation.

10. A method as in claim 9, further comprising the steps of:
    interplanting said harvested seed of said second filial generation with the female parent of the desired hybrid variety;
    identifying and eliminating the unmarked plant members from among said second filial generation at seedling stage;
    identifying and eliminating the male-fertile plant members from among said second filial generation just before flowering stage;
    pollinating the remaining plant members of said second filial generation; and
    when fruit are mature, only harvest the seed from marked male-sterile plants, said harvested seed to form a backcross progeny.

11. A method as in claim 10, wherein said step of pollinating the remaining plant members of said second filial generation is performed by natural open pollination.

12. A method as in claim 9, wherein said self-pollination step is manually performed by transferring pollen from the male flowers of each plant to the female flowers of that same plant.

13. A method as in claim 5, further comprising the steps of: interplanting the marked genetic male-sterile female parent line with the normal female parent line of the desired hybrid variety;
    identifying and eliminating the male-fertile plant members from among the marked genetic male-sterile female parent plants before fruit-setting has occurred;
    naturally cross-pollinating the remaining plant members; and when fruit are mature, only harvest the seed from male-sterile plants.

14. A method as in claim 5, further comprising the step of testing the hybrid seed by visual identification of the cotyledon of the plants grown from said hybrid seed so harvested according to the marker.

15. A method as in claim 14, wherein said testing is completed in less than two weeks.

16. A method as in claim 13, further comprising the step of eliminating the seedlings showing the marked trait and only allowing fruiting of the seedlings lacking the marked trait.

17. A method as in claim 13, wherein the genetic purity of the marked genetic male-sterile female parent line is maintained.

18. A method as in claim 17, wherein the genetic purity of the marked genetic male-sterile female parent line is maintained by propagating the marked genetic male-sterile female parent line in an isolated growing medium and eliminating any wild types before pollen is produced in the flowering stage.

19. A method as in claim 13, wherein the genotype population ratio of one male-sterile to one male-fertile is maintained.

20. A method as in claim 19, wherein the one male-sterile to one male-fertile genotype population ratio is maintained by harvesting only the seed from male-sterile plants of the marked genetic male-sterile female plants.

21. A method as in claim 13, wherein said marker gene is a recessive mutant gene.

22. A method as in claim 13, wherein said marker gene is a conditional recessive mutant gene.

23. A method of producing seed for commercial production of a desired watermelon hybrid plant variety, comprising the steps of:
    identifying a first watermelon line with a suitable male-sterile gene;
    identifying a second watermelon line with a suitable marker gene, said marker gene being disposed with respect to said male-sterile gene in one of the following two relative dispositions, the first of said relative dispositions being on separate chromosomes and the second of said relative dispositions being on the same pair of chromosomes such that said male-sterile gene and said marker gene independently segregate;
    crossing sufficient generations of progeny of said two lines to produce a genetic stock which is double recessive for said male-sterile and marker genes;
    crossing said double recessive as a female parent with a suitable male parent; and
    harvesting hybrid seed from the female parent.

24. A method as in claim 23, further comprising the step of maintaining said double recessive genetic stock.

25. A method as in claim 23, further comprising the step of performing a transfer protocol that uses said double recessive genetic stock to introduce said male-sterile gene and said marker gene into a female parent candidate of a desired hybrid variety and produces a marked genetic male-sterile female parent line.

26. A method as in claim 25, further comprising the steps of interplanting marked genetic male-sterile female parent plants with male parent plants;
    removing visually recognizable male-fertile plants in the marked genetic male-sterile female parent rows before fruit set occurs;
    performing cross-pollination between said marked genetic male-sterile female parent plants and said male parent plants; and
    harvesting seed from said marked genetic male-sterile female parent plants.

27. A method as in claim 26, wherein said interplanting of the marked genetic male-sterile female parent plants with male parent plants occurs in a ratio of two to four rows of marked genetic male-sterile female parent plants to one row of male parent plants.

28. A method as in claim 26, wherein said cross-pollination is performed using bees.

29. A method of producing a double recessive cucurbit genetic stock, comprising the steps of:
    identifying a first cucurbit plant line with a suitable male-sterile gene;
    identifying a second cucurbit plant line with a suitable marker gene, said marker gene being disposed with respect to said male-sterile gene in one of the following two relative dispositions, the first of said relative dispositions being on separate chromosomes and the second of said relative dispositions being on the same pair of chromosomes such that said male-sterile gene and said marker gene independently segregate; and crossing sufficient generations of progeny of said two lines to produce a genetic stock which is double recessive for said male-sterile and marker genes.

30. A method of producing a marked genetic male-sterile female parent line, comprising the steps of:

performing in a cucurbit hybrid plant variety a transfer protocol that introduces by sexual reproduction a male-sterile recessive genetic mutant gene and a recessive marker gene, said marker gene being originally disposed with respect to said male-sterile gene in one of the following two relative dispositions, the first of said relative dispositions being on separate chromosomes and the second of said relative dispositions being on the same pair of chromosomes such that said male-sterile gene and said marker gene independently segregate;

said marker gene expressing itself as an identifiable characteristic in a seedling, into a candidate of the female parent of the desired hybrid variety and back-crossing and selfing sufficient generations of progeny to produce a marked genetic male-sterile female parent line.

31. A method of producing a double recessive watermelon genetic stock, comprising the steps of:

identifying a first cucurbit plant line with a suitable male-sterile gene;

identifying a second cucurbit plant line with a suitable marker gene, said marker gene being disposed with respect to said male-sterile gene in one of the following two relative dispositions, the first of said relative dispositions being on separate chromosomes and the second of said relative dispositions being on the same pair of chromosomes such that said male-sterile gene and said marker gene independently segregate;

crossing sufficient generations of progeny of said two lines to produce a genetic stock which is double recessive for said male-sterile and marker genes.

* * * * *